United States Patent
Frings et al.

(10) Patent No.: US 11,798,691 B2
(45) Date of Patent: Oct. 24, 2023

(54) SYSTEM AND METHOD FOR INFECTIOUS DISEASE NOTIFICATION

(71) Applicant: Siemens Healthcare Diagnostics Inc., Tarrytown, NY (US)

(72) Inventors: Oliver Frings, Erlangen (DE); Eugen Kubala, Erlangen (DE); Maximilian Würstle, Baiersdorf (DE); Dominik Neumann, Erlangen (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/016,563

(22) Filed: Sep. 10, 2020

(65) Prior Publication Data
US 2021/0090749 A1    Mar. 25, 2021

(30) Foreign Application Priority Data

Sep. 24, 2019    (EP) ..................................... 19199183

(51) Int. Cl.
*G16H 50/80*    (2018.01)
*G16H 70/60*    (2018.01)
(Continued)

(52) U.S. Cl.
CPC .............. *G16H 50/80* (2018.01); *G06N 7/01* (2023.01); *G06N 20/00* (2019.01); *G16H 10/40* (2018.01);
(Continued)

(58) Field of Classification Search
CPC ........ G16H 50/80; G16H 70/60; G16H 40/20; G16H 10/40; G16H 10/60; G16H 50/70; G16H 70/40
See application file for complete search history.

(56) References Cited

U.S. PATENT DOCUMENTS 8,090,590 B2 *    1/2012   Fotsch ................... G16H 10/60
                                                            705/2
8,359,223 B2 *    1/2013   Chi .................. G06Q 10/06312
                                                          705/7.22
(Continued)

FOREIGN PATENT DOCUMENTS

WO    WO-2019025901 A1 *    2/2019
WO    WO 2019025901 A1       2/2019
WO    WO 2019165004 A1       8/2019

OTHER PUBLICATIONS

Extended European Search Report for European Application No. 19199183.5 dated Apr. 1, 2020.

*Primary Examiner* — Rajesh Khattar
*Assistant Examiner* — Steven G. S. Sanghera

(57) ABSTRACT

A system is for infectious disease notification. The system includes at least one processor, configured to use a machine learning monitoring algorithm, trained on a large number of EMR datasets of patients, to calculate a probability for an infectious disease from a provided EMR dataset and compare the probability of the provided EMR dataset calculated with a known value. In training of the monitoring algorithm, the value represents whether there was an onset of an infectious disease or not and the monitoring algorithm is designed to adjust parameters of the monitoring algorithm. And in evaluating a notification, the value is a threshold value and the system is designed to output a notification upon the probability being greater than the threshold value.

19 Claims, 2 Drawing Sheets

(51) Int. Cl.
  *G16H 40/20* (2018.01)
  *G16H 10/40* (2018.01)
  *G16H 10/60* (2018.01)
  *G16H 50/70* (2018.01)
  *G16H 70/40* (2018.01)
  *G06N 20/00* (2019.01)
  *G06N 7/01* (2023.01)

(52) U.S. Cl.
  CPC .............. *G16H 10/60* (2018.01); *G16H 40/20* (2018.01); *G16H 50/70* (2018.01); *G16H 70/40* (2018.01); *G16H 70/60* (2018.01)

(56) References Cited

U.S. PATENT DOCUMENTS

| | | | |
|---|---|---|---|
| 9,955,869 B2 * | 5/2018 | Meltzer | A61B 5/0022 |
| 10,249,389 B2 * | 4/2019 | Athey | G16B 20/20 |
| 10,327,697 B1 * | 6/2019 | Stein | G06K 9/66 |
| 2005/0182303 A1 * | 8/2005 | Yancey, Jr. | G16H 20/10 |
| | | | 600/300 |
| 2018/0107926 A1 * | 4/2018 | Choi | G06N 3/0472 |
| 2018/0315494 A1 * | 11/2018 | Kolde | G16H 10/60 |
| 2019/0214138 A1 * | 7/2019 | Aoyagi | G16H 50/70 |
| 2020/0243163 A1 * | 7/2020 | Van Aggelen | G16B 40/20 |

\* cited by examiner

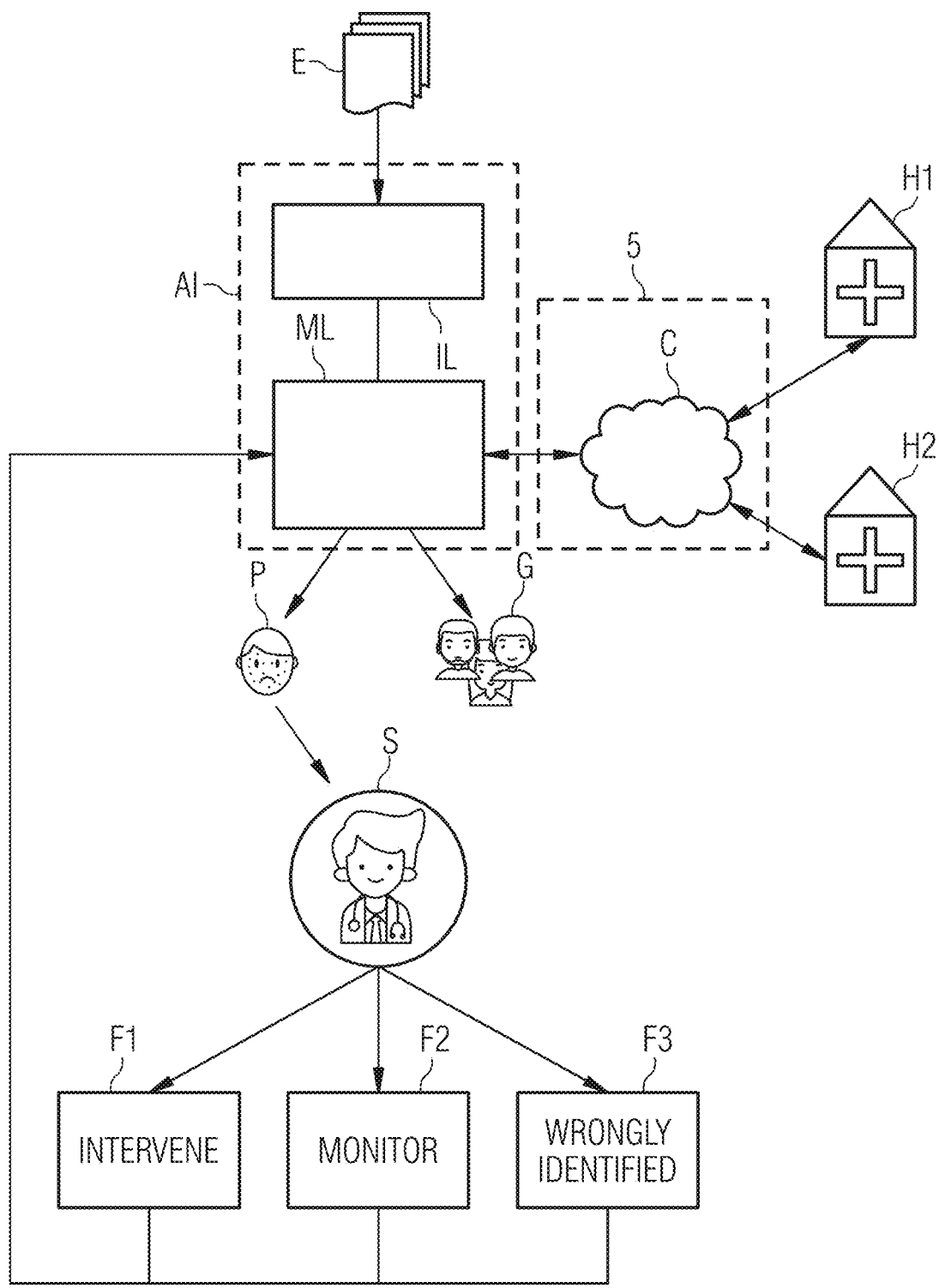

SYSTEM AND METHOD FOR INFECTIOUS DISEASE NOTIFICATION

PRIORITY STATEMENT

The present application hereby claims priority under 35 U.S.C. § 119 to European patent application number EP19199183.5 filed Sep. 24, 2019, the entire contents of which are hereby incorporated herein by reference.

FIELD

Embodiments of the invention generally relate to a system and a method for infectious disease notification, preferably for the notification of a specialist in case of a risk of an infectious disease. Especially, at least one embodiment of the invention describes an artificial intelligence driven infectious disease specialist notification system.

BACKGROUND

Today, a major complication in hospitals is the development of an infection, e.g. a sepsis, in patients that have been hospitalized and underwent medical procedures, e.g. a surgery or a biopsy.

Current workflow is, that the infectious disease specialist is called on demand by the attending physician when a severe infection is suspected or already confirmed. Since severe infections are acute diseases, where time is a critical factor, the infections disease specialist is often called too late. This can cause delaying in the correct treatment of the infection and worsen the patient outcome. Therefore, it is critical that the infectious disease specialist is informed as soon as possible.

Currently, there is no technical solution in a hospital to automatically inform the infectious disease specialist at an earlier time point.

SUMMARY

At least one embodiment of the present invention is directed to improving the known systems and methods to facilitate an improvement in preventing complications due to infectious diseases, by infectious disease notification.

Embodiments of the present invention are directed to a system; a method and a network service system.

A system according to at least one embodiment of the invention serves for infectious disease notification, i.e. a notification about the probability of an onset of an infectious disease. To determine the probability of an onset of an infectious disease, a prediction is necessary that is based on current data of a patient. This data is further called "patient-data" and comprises data from the EMR (electronic medical record) of the patient, preferably from the group of vital signs, lab results, point of care test results, patient care related procedures, other procedures, comorbidities, patient history, patient demographics, other diseases and clinical care data.

A method according to at least one embodiment of the invention for infectious disease notification works with a system according to the invention and uses an EMR dataset of a patient provided to the system. The method comprises:
  calculating a probability for an infectious disease from the EMR dataset with the system. Since the system is designed for this task, this is done automatically after the system gets the EMR dataset;
  comparing the calculated probability of a provided EMR dataset with a predefined threshold value. As said above, the threshold value is a probability value comparable with the probability; and
  outputting a notification, e.g. an alert, if the probability lies over the threshold. Preferably an infectious disease specialist is notified (direct via a data connection).

At least one embodiment of the invention is also achieved by a computer program product with a computer program that is directly loadable into the memory of a device of a system, and which comprises program units to perform the steps of at least one embodiment of at least one embodiment of the inventive method when the program is executed by the system. In addition to the computer program, such a computer program product can also comprise further parts such as documentation and/or additional components, also hardware components such as a hardware key (dongle etc.) to facilitate access to the software.

At least one embodiment of the invention is directed to a computer readable medium such as a memory stick, a hard-disk or other transportable or permanently-installed carrier can serve to transport and/or to store the executable parts of the computer program product so that these can be read from a processor unit of a system. A processor unit can comprise one or more microprocessors or their equivalents.

According to a preferred method of at least one embodiment, the monitoring algorithm is further trained when a new EMS dataset of a patient is added to the system, comprising:
  calculating a probability for an infectious disease from the EMR dataset with the system;
  comparing the calculated probability of a provided EMR dataset with a value representing whether there was an onset of an infectious disease or not; and
  adjusting the parameters of the monitoring algorithm accordingly.

Thus, according to a preferred method of an embodiment, the system is further trained when a new feedback of a specialist is added to the system, comprising:
  calculating a probability for an infectious disease from the EMR dataset connected with the feedback with the system;
  comparing the calculated probability of a provided EMR dataset with a value representing whether there was an onset of an infectious disease or not based on the feedback; and adjusting the parameters of the monitoring algorithm accordingly.

At least one embodiment of the invention is directed to a system for infectious disease notification comprising:
  at least one processor, configured to use a machine learning monitoring algorithm, trained on a large number of EMR datasets of patients, to
    calculate a probability for an infectious disease from a provided EMR dataset, and
    compare the probability of the provided EMR dataset calculated with a known value,
  wherein in training of the monitoring algorithm, the value represents whether there was an onset of an infectious disease or not and the monitoring algorithm is designed to adjust parameters of the monitoring algorithm accordingly, and
  wherein in evaluating a notification, the value is a threshold value and the system is designed to output a notification upon the probability being greater than the threshold value.

At least one embodiment of the invention is directed to a method for infectious disease notification with a system, using a machine learning monitoring algorithm, trained on a large number of EMR datasets of patients, from a EMR dataset of a patient provided to the system, the method comprising:

calculating a probability for an infectious disease from the EMR dataset with the system;

comparing the probability of the EMR dataset calculated, with a threshold value; and outputting a notification upon the probability lying above the threshold value.

At least one embodiment of the invention is directed to a non-transitory computer program product storing a computer program, directly loadable into a computing device, including program elements for performing the method of an embodiment when the computer program is executed by the computing device.

At least one embodiment of the invention is directed to a non-transitory computer-readable medium storing program elements, readable and executable by a computer unit, to perform the method of an embodiment when the program elements are executed by the computer unit.

BRIEF DESCRIPTION OF THE DRAWINGS

Other objects and features of the present invention will become apparent from the following detailed descriptions considered in conjunction with the accompanying drawings. It is to be understood, however, that the drawings are designed solely for the purposes of illustration and not as a definition of the limits of the invention.

FIG. 3 depicts a preferred inner architecture of a system according to an embodiment of the invention and the flow of information.

In the diagrams, like numbers refer to like objects throughout. Objects in the diagrams are not necessarily drawn to scale.

DETAILED DESCRIPTION OF THE EXAMPLE EMBODIMENTS

Figure 1:
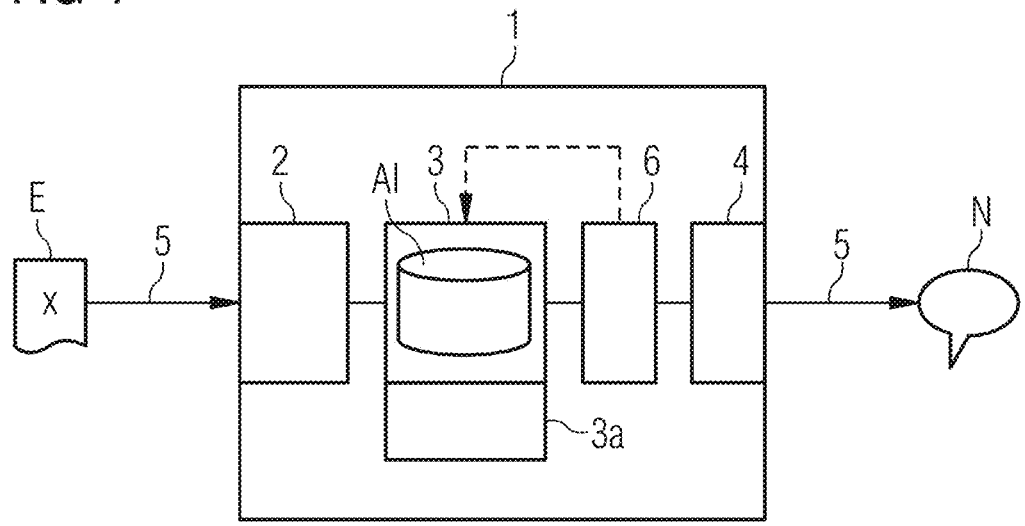
FIG. 1 shows a simplified system according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A system according to at least one embodiment of the invention serves for infectious disease notification, i.e. a notification about the probability of an onset of an infectious disease. To determine the probability of an onset of an infectious disease, a prediction is necessary that is based on current data of a patient. This data is further called "patient-data" and comprises data from the EMR (electronic medical record) of the patient, preferably from the group of vital signs, lab results, point of care test results, patient care related procedures, other procedures, comorbidities, patient history, patient demographics, other diseases and clinical care data.

An idea of at least one embodiment of the invention is that the monitoring algorithm analyses patients with infectious diseases present in the hospital and distinguishes the ones which might develop severe infection. Those patients are then preferably reported to the Infectious diseases specialist who then may contact the primary attending physician, e.g. an oncologist or a cardiologist. Currently, it is the other way round: the primary attending physician contacts the infectious diseases specialist for help if a disease is determined. It should be noted that although it is preferred to automatically connect the specialist directly (e.g. via a predefined address and a notification sent to this address), it is also possible that the notification is sent or displayed to the staff who then call the specialist.

The system of at least one embodiment comprises a machine learning monitoring algorithm being trained on a large number of EMR datasets of patients and preferably also current epidemiology profiles of medical institutions. Very important data are the antibiotics used, outcomes (e.g.

length of disease), biochemistry and vital signs of the previous patients. The monitoring algorithm is designed such that it calculates a probability for an infectious disease from any provided EMR dataset (during training as well as during normal performance), and the system is designed to compare the calculated probability of a provided EMR dataset with a known value. The comparison can be achieved by the monitoring algorithm or by a separate comparison unit.

There are (at least) two possible work modes of the system: training and evaluating a notification.

In the course of training, the (known) value represents whether there was an onset of an infectious disease or not ("ground truth") and the monitoring algorithm is designed for adjusting its parameters accordingly. This may be achieved e.g. in that the monitoring algorithm calculates a probability with its predefined parameters, validates the result on basis of the ground truth and if the result does not match ameliorates the parameters as long as the result lies in a predefined range around the ground truth.

In the course of evaluating a notification, the value is a predefined threshold value (or short "threshold") and the system is designed to output a notification in the case the probability lies over the threshold, i.e. if the calculated probability lies over the threshold. It is clear that the threshold is a probability threshold e.g. 70%. Thus, once the risk prediction feature of the algorithm reaches a defined threshold of certainty for a patient to either develop a severe infection or having already a non-diagnosed/discovered severe infection, a notification is issued.

It is preferred that the notification is used to inform an infections disease specialist. Thus, the specialist is preferably informed with the notification by the system automatically. Preferably, the notification includes all relevant and up-to date clinical information of that patient, allowing the infectious disease specialist to determine the status of the patient. If necessary, then clinical actions need to be started such as further diagnostic procedures or treatments. The creation of the notification can be achieved by the monitoring algorithm itself or by a separate notification unit.

The threshold $\tau$ could be set to fixed value, but it is preferred that it can be adjusted, e.g. by a user, so the user can manually tune the sensitivity of the system. As an alternative or addition, the threshold can be learned automatically.

The system of at least one embodiment is preferably used to drive an alarm system to alert an infectious disease specialist. Regarding hardware issues, the system can be realized as a server or another computing system with a processor, a data interface and a memory, wherein the monitoring algorithm runs in the environment of the processor and the EMR datasets are provided via the data interface and/or being saved in the memory. The data interface is preferably connected to a data network as e.g. a medical data network or the internet. The inner architecture of the monitoring algorithm is preferably an input layer receiving the EMR datasets and a monitoring layer comprising the functional and self-learning part of the algorithm.

At least one embodiment of the invention can be for instance part of an integrated decision support system for infectious diseases, such as AI-PC Infection.

A method according to at least one embodiment of the invention for infectious disease notification works with a system according to at least one embodiment of the invention and uses an EMR dataset of a patient provided to the system.

At least one embodiment of the method comprises:
calculating a probability for an infectious disease from the EMR dataset with the system. Since the system is designed for this task, this is done automatically after the system gets the EMR dataset;
comparing the calculated probability of a provided EMR dataset with a predefined threshold value. As said above, the threshold value is a probability value comparable with the probability; and
outputting a notification, e.g. an alert, if the probability lies over the threshold. Preferably an infectious disease specialist is notified (direct via a data connection).

A network service system according to at least one embodiment of the invention comprises a system according to the invention and/or is designed for performing a method according to at least one embodiment of the invention. It is preferably a cloud service.

Some units or modules of the system mentioned above can be completely or partially realized as software modules running on a processor of a device. A realization largely in the form of software modules can have the advantage that applications already installed on an existing system can be updated, with relatively little effort, to install and run these units of the present application.

At least one embodiment of the invention is also achieved by a computer program product with a computer program that is directly loadable into the memory of a device of a system, and which comprises program units to perform the steps of at least one embodiment of at least one embodiment of the inventive method when the program is executed by the system. In addition to the computer program, such a computer program product can also comprise further parts such as documentation and/or additional components, also hardware components such as a hardware key (dongle etc.) to facilitate access to the software.

At least one embodiment of the invention is directed to a computer readable medium such as a memory stick, a hard-disk or other transportable or permanently-installed carrier can serve to transport and/or to store the executable parts of the computer program product so that these can be read from a processor unit of a system. A processor unit can comprise one or more microprocessors or their equivalents.

Particularly advantageous embodiments and features of the invention are given by the claims, as revealed in the following description. Features of different claim categories may be combined as appropriate to give further embodiments not described herein.

According to a preferred system of at least one embodiment, the monitoring algorithm is a regression model, that is preferably a continuously learning regression model. This regression model is preferably based on regularized regression models (such as e.g. lasso, or elastic net), random forest, support vector machines or deep neural networks. Surely, the regression model is parameterized accordingly with suitable parameters $\theta$. The continuously learning regression model could provide a mapping f (with parameters $\theta$) that takes as input the complete data x of the EMR dataset available for a patient, and computes as its output a probability y representing the likelihood of the patient to develop a severe infection. In short this would mean $f(x;\theta)=y$.

For neural networks, for example, the parameters $\theta$ would be the weights for each of the neurons' connections, or even including the network architecture (number of layers and/or neurons and/or connections, type of layers, etc.

The monitoring algorithm preferably takes patient centric information as well as clinical information into account.

Thus, according to a preferred system, the monitoring algorithm is designed to process EMR data from the group of vital signs, lab results, point of care test results, patient care related procedures, other procedures, comorbidities, patient history, patient demographics, other diseases and clinical care data. It should be noted that the monitoring algorithm requires a retrospective data set of patients for initial training. This initial training set can come from either another hospital or if available from the hospital that already uses at least one embodiment of the invention.

A preferred system of at least one embodiment, comprises a data connection to more than one medical institution (e.g. a number of hospitals and/or research facilities) and is designed to receive EMR datasets from the medical institutions. It should be noted that in order to improve predictiveness of the monitoring algorithm a larger data set could be used. If one hospital alone does not provide enough data, data from other hospitals using the same software solution are preferably integrated in the learning process.

A preferred system of at least one embodiment, comprises an input interface for a data network or an input device for receiving marking data, wherein the system is designed to mark a EMR dataset or identification data of a patient, especially with flags indicating that there is the risk of an infection, that the patient needs further monitoring or that a patient is wrongly flagged. Correspondingly, according to a preferred method, an EMR dataset or identification data of a patient is marked (by a specialist or another user). The marking is preferably made manually, however, it is also possible that it is done automatically by a device examining the patient.

Especially in the case a disease specialist determines that a patient doesn't require an intervention yet, but needs further monitoring, the patient may be flagged (i.e. a mark) for further monitoring. The system is preferably designed such that it considers this flag as another evaluation of this patient after a predefined time or a time given by the flag. In addition, a flag can be used to inform attending clinical staff.

There may be the case that a disease specialist determines that a patient is wrongly flagged. For example a patient is flagged with a high risk of a severe infectious disease (e.g. by the system), but is not after examination. This it is preferred that the specialist has a possibility to flag this error as well. Thus, the mark preferably comprises flags indicating that there is the risk of an infection, that the patient needs further monitoring or that a patient is wrongly flagged.

According to a preferred system of at least one embodiment, the monitoring algorithm is designed to be trained on previous cases as well as a current epidemiology profile of a hospital, preferably on data pertaining to the group of medication, especially antibiotics used; outcomes, especially length of a disease; biochemistry and vital signs (of the previous patients).

In a preferred system according to the invention of at least one embodiment, components of the system are part of a data-network, wherein the data-network preferably comprises parts of the internet and/or a cloud-based computing system, wherein preferably the system according to of at least one embodiment the invention is realized in this cloud-based computing system. For example, the components of the system are part of a data-network, wherein preferably the data-network and a medical imaging system which provides the image data are in communication with each other. Such a networked solution could be implemented via an internet platform and/or in a cloud-based computing system.

The method may also include elements of "cloud computing". In the technical field of "cloud computing", an IT infrastructure is provided over a data-network, e.g. a storage space or processing power and/or application software. The communication between the user and the "cloud" is achieved via data interfaces and/or data transmission protocols.

In the context of "cloud computing", in a preferred embodiment of the method according to the invention, provision of data via a data channel (for example a data-network) to a "cloud" takes place. This "cloud" includes a (remote) computing system, e.g. a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

Within the scope of a preferred embodiment of the system according to the invention, the abovementioned units (data interface, memory, computing unit, comparison unit, notification unit) Are present on the "cloud" side. A preferred system further comprises, a local computing unit connected to the system via a data channel (e.g. a data-network, particularly configured as RIS or PACS). The local computing unit includes at least one data receiving interface to receive data. Moreover, it is preferred if the local computer additionally has a transmission interface in order to send data to the system.

According to a preferred method of at least one embodiment, the monitoring algorithm is further trained when a new EMS dataset of a patient is added to the system, comprising:
    calculating a probability for an infectious disease from the EMR dataset with the system;
    comparing the calculated probability of a provided EMR dataset with a value representing whether there was an onset of an infectious disease or not; and
    adjusting the parameters of the monitoring algorithm accordingly.

It should be noted that since the parameters are possibly amended, it is preferred that the monitoring algorithm is trained on a number of EMR datasets (the large number of datasets mentioned above or at least a part of this large number of datasets) including the new EMR dataset. The more EMR datasets are used the more advantageous for the accuracy of the parameters.

It is preferred in an embodiment, that the feedback of an infectious disease specialist is taken into account by the monitoring algorithm to further improve the predictive accuracy.

Thus, according to a preferred method of an embodiment, the system is further trained when a new feedback of a specialist is added to the system, comprising:
    calculating a probability for an infectious disease from the EMR dataset connected with the feedback with the system;
    comparing the calculated probability of a provided EMR dataset with a value representing whether there was an onset of an infectious disease or not based on the feedback; and
    adjusting the parameters of the monitoring algorithm accordingly.

It should be noted that since the parameters could be amended, it is preferred that the monitoring algorithm is trained on a number of EMR datasets (the large number of datasets mentioned above or at least a part of this large number of datasets) including the new feedback of a specialist. The more EMR datasets are used the more advantageous for the accuracy of the parameters.

According to a preferred method of an embodiment, the monitoring algorithm is a regression model with parameters θ that are in the course of training with a number of n training EMR datasets x of patients where a ground truth z is known whether they developed an infection in a given time period (z=1) or not (z=0), while calculating the probability f(x) of an infection in the given time period, wherein the parameters θ of the regression model that will minimize the error between the calculated probability y and the ground truth outcome z are calculated with the formula θ=armin θ' Σ(dist(f(x;θ'),z)), wherein the sum runs over the n EMR datasets and wherein the function dist is a norm, preferably the absolute or squared difference between the two values f(x) and z.

It is advantageous that training data is split in training and validation/testing data, in order to avoid overfitting and support generalizability of the learned model.

It is preferred that a retrospective training set is used to learn an initial regression model, which enables the monitoring system to generate notification (e.g. alerts) if a new patient gets into a state of high risk of an infectious disease. However, the high risk alerts might not always be correct, especially when new patients whose data that significantly deviates from the training data population are analyzed. Therefore, it is advantageous to continuously update the parameter vector θ by solving the minimization problem defined above every time new data and/or specialist feedback is available (see above). Next time a patient is analyzed, the new model can immediately be applied to get an improved risk prediction based also on new EMR datasets or specialist feedback.

However, there could appear the case that the types and amount of available patient data might not be comparable for all patients, and some data might be missing. To compensate this, preferably respective EMR datasets are prepared.

According to a preferred method of an embodiment, as a preprocessing step, data of an EMR dataset is normalized such that it is always represented in the same way, required for the regression model input.

Additionally or alternatively, data imputation methods are applied on a part of an EMR dataset where there are missing values, e.g. by filling missing values with population-averages, or similar. It is preferred that representation learning methods are applied as tools to bring the data into a proper representation. Preferred is an advanced presentation, that also aids solving the task of identifying infection risks.

The monitoring algorithm could need corrections for all attributes of different patients. For example the normalization of the biochemistry and vital values for patients since there are different for male, female, children patients or patients with comorbidities as obesity, cancer or one kidney.

It is preferred in the case new data and new patients are added, not only to train the monitoring algorithm again (see above), but also reconsider the preprocessing, in particular to recompute an optimal data representation that better takes into account the newly added information. This could also be triggered automatically and, for example for neural network based regression, the shape of the input layer could automatically be adapted to the newly updated representation.

FIG. 1 shows a simplified system 1, that can be e.g. a server 1/cloud service, for a data network 5 according to an embodiment of the invention. The system 1 comprises a data-interface 2 designed for receiving EMR datasets E over the network 5, a computing unit 3 with a memory 3a (the memory 3a designed for saving data or for providing RAM), a comparison unit 6 and a notification unit 4. The notification unit 4 creates a notification N and can be designed as a data interface to send the notification N over the data network 5 as shown here or it is a unit that uses a data interface, e.g. the shown data interface 2 to send the notification N over the data network 5 (e.g. to a specialist).

The computing unit 3 is designed to train and execute a machine learning monitoring algorithm AI running as a process. The monitoring algorithm AI is the "heart" of the system 1 and trained on a large number of EMR datasets of patients and current epidemiology profiles of medical institutions. It is designed such that it calculates a probability PV (a probability value) for an infectious disease from any provided EMR dataset E.

The comparison unit 6 then compares the calculated probability PV of a provided EMR dataset with a known value (see e.g. FIG. 1). This comparison may also be achieved by the monitoring algorithm AI or the comparison unit 6 may be part of the monitoring algorithm AI. The comparison unit 6 could be part of the notification unit 4.

In the course of its normal work, i.e. the evaluation of a notification, the comparison unit 6 compares the probability PV with a predefined threshold value T and the notification unit 4 outputs a notification N if the probability lies over the threshold value T. While the notification N may be a standardized dataset, the notification unit 4 can add data necessary for an examination by the specialist or create an alert message. The notification unit 4 may also act as data interface. It should be noted that the notification unit 4 may also be a part of the monitoring algorithm AI.

In the course of training, the value represents whether there was an onset of an infectious disease or not and after comparison with the comparison unit 6, the monitoring algorithm AI adjusts its parameters accordingly (indicated by the dashed arrow pointing back to the computing unit 3).

Figure 2:
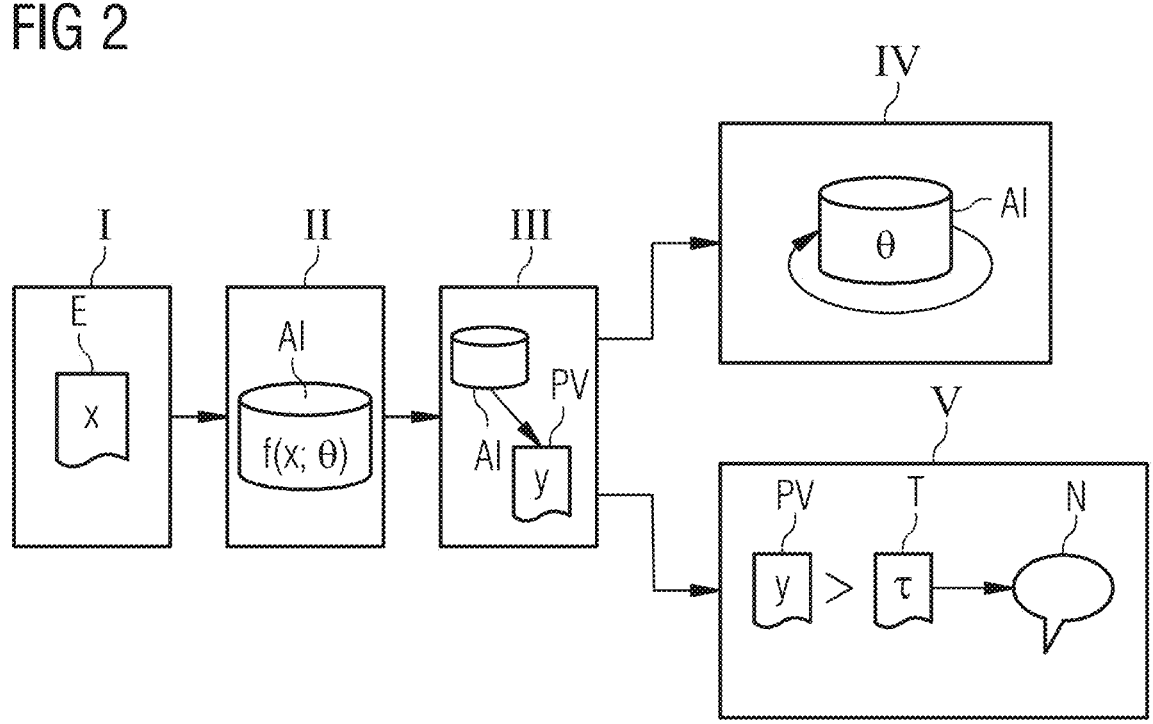
FIG. 2 shows a diagram of the process flow of a preferred method of an embodiment according to the invention.

FIG. 2 shows a diagram of the process flow of a preferred method according to an embodiment of the invention for infectious disease notification using a system 1 as e.g. shown in FIG. 1.

In step I, an EMR dataset E of a patient is provided to the system 1. This may be achieved by sending the EMR dataset E via a data network 5 (e.g. a PACS, a Picture Archiving and Communication System or the internet) to the system 1, which receives the EMR dataset E with the data interface 2.

In step II, a probability for an infectious disease is calculated from the EMR dataset E by the system 1. Since the system 1 comprises a trained monitoring algorithm AI, the calculation is done automatically.

In step III, the calculated probability of a provided EMR dataset is now calculated and provided by the monitoring algorithm AI.

Now, there are two possibilities. Step IV shows a step in the training state. This state is surely used at the initial training of the monitoring algorithm AI, but may be used later on to improve the monitoring algorithm AI by further learning by using new EMR datasets. Step V shows a step in the working state, where the system 1 does what it should do, i.e. create a notification.

In step IV, the monitoring algorithm AI of the system 1 is further trained when a new EMS dataset E of a patient P is added to the system 1. This is achieved by calculating a probability PV for an infectious disease from the EMR dataset E with the monitoring algorithm AI of the system 1

(already done in steps II and III, but done several times during training), comparing the calculated probability PV with a value representing whether there was an onset of an infectious disease or not and adjusting the parameters of the monitoring algorithm AI accordingly. It is preferred that the additional training is done with a vast number of EMR datasets E including the new EMR dataset E (and/or a feedback of a specialist S).

In step V, the calculated probability PV is compared with a predefined threshold value T and a notification N is issued in the case that the probability lies over the threshold.

FIG. 3 shows the inner architecture of a system 1 according to an embodiment of the invention (see e.g. FIG. 2) and depicts the flow of information.

The monitoring algorithm here comprises an input layer IL receiving EMR datasets E and a (self learning) monitoring layer ML calculating probabilities (and especially comparing these probabilities with a value). The monitoring layer ML in this example has a data connection to a cloud structure C in a data network 5, and over this cloud data contact to further hospitals H1, H2, as medical institution H1, H2 in order to receive further EMR datasets for training or metadata.

The data that is extracted from the EMR datasets E by the input layer may be from the group of vital signs, lab results, point of care test results, patient care related procedures, other procedures, comorbidities, patient history, patient demographics, other diseases and clinical care data. The monitoring algorithm AI uses an EMR dataset E of a patient P and is trained on EMR datasets E of a (vast) group of patients G.

The result (a notification, see e.g. FIG. 1 or 2) is sent to an infection disease specialist S and flagged with flags F1, F2, F3 (marks F1, F2, F3). The images of the patient P and the group of patients G stands for the result of the monitoring layer ML. The specialist S is only notified about patient P, not about the patient group G, since there is no critical result here. The specialist S then decides what to do with the patient P while flagging the result. One flag F1 may indicate a necessity to intervene, one flag F2 may indicate a necessity to monitor a patient P and one flag F3 may indicate a wrongly identified risk for disease.

The arrow pointing back from the flags F1, F2, F3 to the monitoring layer should indicate that the feedback of the specialist is another source for training the monitoring algorithm AI.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The mention of a "unit" or a "system" does not preclude the use of more than one unit or system.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A system for infectious disease notification comprising:
at least one processor, configured to use a machine learning monitoring algorithm, trained on a large number of electronic medical record (EMR) datasets of previous cases of patients, to
apply data imputation methods on a part of a provided EMR dataset where there are missing values, to bring the data into a proper representation,
calculate a probability value for an infectious disease from the provided EMR dataset,
compare the probability value of the provided EMR dataset calculated with a known value,
output a notification upon the probability value lying above the known value,
train the monitoring algorithm, wherein in training of the monitoring algorithm, the known value represents whether there was an onset of an infectious disease or not and the monitoring algorithm iteratively adjusts parameters of the monitoring algorithm, and
evaluate a notification based on the adjusted parameters, wherein in evaluating the notification, the known value is a threshold value and the system is designed to output the notification upon the probability value being greater than the threshold value, wherein the monitoring algorithm is trained on the previous cases of patients and a current epidemiology profile of a hospital, the epidemiology profile of the hospital comprising data pertaining to a group of medication, including antibiotics, used within the hospital, and
wherein the monitoring algorithm is a regression model with parameters θ that are, in a course of training with a number of n training EMR datasets x of patients where a ground truth z is known whether the patients developed an infection in a given time period or not, while calculating the probability (PV) y=f(x) of an infection in a given time period, wherein the parameters θ of a regression model to minimize error between the probability calculated y and the ground truth outcome z are calculated with $$\theta=\text{argmin}_\theta \Sigma(\text{dist}(f(x;\theta'),z)),$$

wherein a sum Σ runs over the n EMR datasets and wherein the function dist is an absolute or squared difference between the two values f(x) and z.

2. The system of claim 1, wherein the monitoring algorithm is a regression model.

3. The system of claim 1, wherein the monitoring algorithm is designed to process at least one of EMR data of a group vital signs, lab results, point of care test results, patient care related procedures, co-morbidities, other diseases and clinical care data.

4. The system of claim 1, further comprising:
a data connection to more than one medical institution, the system being designed to receive EMR datasets from the more than one medical institution, wherein the at least one processor trains the monitoring algorithm using the received EMR datasets.

5. The system of claim 1, further comprising:
an input interface for a data network or an input device for receiving marking data.

6. A method for infectious disease notification with a system, using a machine learning monitoring algorithm, trained on a large number of electronic medical records (EMR) datasets of previous cases of patients, from an EMR dataset of a patient provided to the system, the method comprising:
applying data imputation methods on a part of an EMR dataset where there are missing values, to bring the data into a proper representation;
providing a machine learning monitoring algorithm;
calculating a probability for an infectious disease from the EMR dataset with the machine learning monitoring algorithm of the system;
comparing the probability of the EMR dataset calculated, with a threshold value;
training the machine learning monitoring algorithm based on the previous cases of patients and a current epidemiology profile of a hospital, the epidemiology profile of the hospital comprising data pertaining to a group of medication, including antibiotics, used within the hospital, wherein in training of the monitoring algorithm, the threshold value represents whether there was an onset of an infectious disease or not and the monitoring algorithm iteratively adjusts parameters of the monitoring algorithm;
evaluating a notification based on the adjusted parameters; and
outputting a notification upon the probability lying above the threshold value, and wherein the monitoring algorithm is a regression model with parameters θ that are, in a course of training with a number of n training EMR datasets x of patients where a ground truth z is known whether the patients developed an infection in a given time period or not, while calculating the probability (PV) y=f(x) of an infection in a given time period, wherein the parameters θ of a regression model to minimize error between the probability calculated y and the ground truth outcome z are calculated with $$\theta=\text{argmin}_\theta \Sigma(\text{dist}(f(x;\theta'),z)),$$

wherein a sum Σ runs over the n EMR datasets and wherein the function dist is an absolute or squared difference between the two values f(x) and z.

7. The method of claim 6, wherein the monitoring algorithm of the system is further trained when a new EMS dataset of a patient is added to the system, the further training comprising:
calculating a probability for an infectious disease from the EMR dataset with the system;
comparing the probability of the EMR dataset calculated with a value representing whether there was an onset of an infectious disease or not; and
adjusting parameters of the monitoring algorithm based upon the comparing.

8. The method of claim 6, wherein the monitoring algorithm of the system is further trained when a feedback of a specialist is added to the system, the further training comprising:
calculating a probability for an infectious disease from the EMR dataset connected with the feedback with the system;
comparing the probability of the EMR dataset calculated with a value representing whether there was an onset of an infectious disease or not based on the feedback; and
adjusting parameters of the monitoring algorithm based upon the comparing.

9. The method of claim 6, wherein an EMR dataset or identification data of a patient is marked.

10. The method of claim 6, further comprising:
a preprocessing step, wherein data of the EMR dataset is normalized to always be represented in a same way, required for the regression model input.

11. A network service system, comprising
a system for infectious disease notification including:
at least one processor, configured to use a machine learning monitoring algorithm, trained on a large number of electronic medical record (EMR) datasets of previous cases of patients, to
apply data imputation methods on a part of a provided EMR dataset where there are missing values, to bring the data into a proper representation,
calculate a probability value for an infectious disease from the provided EMR dataset,
compare the probability value of the provided EMR dataset calculated with a known value,
output a notification upon the probability value lying above the known value, and
train the monitoring algorithm, wherein in training of the monitoring algorithm, the known value represents whether there was an onset of an infectious disease or not and the monitoring algorithm iteratively adjusts parameters of the monitoring algorithm, and
evaluate a notification based on the adjusted parameters, wherein in evaluating the notification, the known value is a threshold value and the system is designed to output the notification upon the probability value being greater than the threshold value, wherein the monitoring algorithm is trained on the previous cases of patients and a current epidemiology profile of a hospital, the epidemiology profile of the hospital comprising data pertaining to a group of medication, including antibiotics, used within the hospital, and wherein the monitoring algorithm is a regression model with parameters θ that are, in a course of training with a number of n training EMR datasets x of patients where a ground truth z is known whether the patients developed an infection in a given time period or not, while calculating the probability (PV) y=f(x) of an infection in a given time period, wherein the parameters θ of a regression model to minimize error between the probability calculated y and the ground truth outcome z are calculated with $$\theta = \mathrm{argmin}_\theta \Sigma(\mathrm{dist}(f(x;\theta'),z)),$$

wherein a sum Σ runs over the n EMR datasets and wherein the function dist is an absolute or squared difference between the two values f(x) and z.

12. A non-transitory computer program product storing a computer program, directly loadable into a computing device, including program elements for performing the method of claim 6 when the computer program is executed by the computing device.

13. A non-transitory computer-readable medium storing program elements, readable and executable by a computer unit, to perform the method of claim 6 when the program elements are executed by the computer unit.

14. The system of claim 2, wherein the monitoring algorithm is a regression model that is a continuously learning regression model.

15. The system of claim 14, wherein the continuously learning regression model is based on regularized regression models, random forest, support vector machines or deep neural networks.

16. The system of claim 5, wherein the system is designed to mark the EMR dataset or identification data of the patient with flags indicating that there is the risk of an infection, that the patient needs further monitoring or that the patient is wrongly flagged.

17. The system of claim 1, wherein the monitoring algorithm is designed to be trained on data pertaining to the group of medication used, outcomes, biochemistry and vital signs.

18. The method of claim 7, wherein the monitoring algorithm of the system is further trained when a feedback of a specialist is added to the system, the further training comprising:
    calculating a probability for an infectious disease from the EMR dataset connected with the feedback with the system;
    comparing the probability of the EMR dataset calculated with a value representing whether there was an onset of an infectious disease or not based on the feedback; and
    adjusting the parameters of the monitoring algorithm based upon the comparing.

19. The method of claim 9, wherein an EMR dataset or identification data of a patient is marked with flags indicating that the patient needs further monitoring or that a patient is wrongly flagged.

* * * * *